(12) United States Patent
Zapolsky et al.

(10) Patent No.: US 9,067,940 B2
(45) Date of Patent: Jun. 30, 2015

(54) ALICYCLIC DERIVATIVES OF N,N'-SUBSTITUTED 3,7-DIAZABICYCLO[3.3.1]NONANES AND MEDICAMENTS BASED THEREON

(76) Inventors: Maxim Eduardovich Zapolsky, Moscow region (RU); Nikolay Serafimovich Zefirov, Moscow (RU); Vladimir Alexandrovich Palyulin, Moscow (RU); Mstislav Igorevich Lavrov, Moscow (RU)

( * ) Notice: Subject to any disclaimer, the term of this patent is extended or adjusted under 35 U.S.C. 154(b) by 5 days.

(21) Appl. No.: 14/113,558

(22) PCT Filed: Apr. 10, 2012

(86) PCT No.: PCT/RU2012/000267
§ 371 (c)(1),
(2), (4) Date: Oct. 23, 2013

(87) PCT Pub. No.: WO2012/148308
PCT Pub. Date: Nov. 1, 2012

(65) Prior Publication Data
US 2014/0046067 A1 Feb. 13, 2014

(30) Foreign Application Priority Data
Apr. 26, 2011 (RU) ................................ 2011116323

(51) Int. Cl.
*C07D 471/08* (2006.01)
*A61K 31/4995* (2006.01)
(52) U.S. Cl.
CPC .......... *C07D 471/08* (2013.01); *A61K 31/4995* (2013.01)
(58) Field of Classification Search
CPC .................................................... C07D 471/08
USPC ................................................. 546/122, 123
See application file for complete search history.

(56) References Cited

U.S. PATENT DOCUMENTS

2004/0147505 A1 7/2004 Peters et al.

FOREIGN PATENT DOCUMENTS

| RU | 2333211 C1 | 9/2008 |
| RU | 2009126653 C2 | 1/2011 |
| WO | 2006087306 A2 | 8/2006 |

OTHER PUBLICATIONS

Adam Doble / The Role of Excitotoxicity in Neurodegenerative Disease: Implications for Therapy // Pharmacology and Therapeutics, 1999, V. 81, N 3, pp. 163-221.
Daniel T. Monaghan, Deborah Yao And Carl W. Cotman / Distribution of [pH] AMPA binding sites in rat brain as determined by quantitative autoradiography // Brain Res., 1984, V. 324, pp. 160-164.
Amy Arai and Gary Lynch / Factors regulating the magnitude of long-term potentiationinduced by theta pattern stimulation // Brain Res., 1992, V. 598, pp. 173-184.
H. Lassmann, R. Weiler, P. Fischer, C. Bancher, K. Jellinger, E. Floor, W. Danielczyk, F. Seitelberger And H. Winkler / Synaptic pathology in alzheimer's disease: immunological data for markers of synaptic and large dense-core vesicles // Neuroscience, 1992, V. 46, pp. 1-6.
Richard Granger, Ursula Staubli, Mike Dams, Yael Perez, Lena Nilsson, Gary A. Rogers, And Gary Lynch / A Drug That Facilitates Glutamatergic Transmission Reduces Exploratory Activity and Improves Performance in a Learning Dependent Task // Synapse, 1993, V. 15, pp. 326-329.
Amy Arai a, Markus Kessler, Peng Xiao, Jos Ambros-Ingerson , Gary Rogers, Gary Lynch // A centrally active drug that modulates AMPA receptor gated currents // Brain Res., 1994, V. 638, pp. 343-346.
I. Ito, S. Tanabet, A. Kohda and H. Sugiyama / Allosteric potentiation of quisqualate receptors by a Nootropic drug aniracetam // J. PhysioL, 1990, V. 424, pp. 533-543.
U. Staubli, M. Kessler, G.Lynch / Aniracetam has proportionately smaller effects on synapses expressing long-term potentiation: Evidence that receptor changes subserve LTP // Psychobiology, 1990, 18(4), pp. 377-381.
Peng Xiao, Ursula Staubli, Markus Kessler, and Gary Lynch / Selective Effects of Aniracetam Across Receptor Types and Forms of Synaptic Facilitation in Hippocampus // Hippocampus, 1991, V.1, pp. 373-380.
A. Guenzi and M. Zanetti / Determination of aniracetam and its main metabolite, N-anisoyl-GABA, in human plasma by high-performance liquid chromatography // J. Chromatogr., 1990, V. 530, pp. 397-406.
Ursula Staubli, Yael Perez, Fangbo Xu, Gary Rogerstt, Martin Ingvar, Sharon Stone-Elander and Gary Lynch / Centrally active modulators of glutamate receptors facilitate the induction of long-term potentiation in vivo // PNAS, 1994, V. 91 pp. 11158-11162.
B. Legutko, X. Li, P. Skolnick / Regulation of BDNF expression in primary neuron culture by LY392098, a novel AMPA receptor potentiator // Neuropharmacology, 2001, V. 40, pp. 1019-1027.
M. Ebadi, R. M. Bashir, M. L. Heidrick, F. M. Hamada, H. El Refaey, A. Hamed, G. Helal, M. D. Baxi, D. R. Cerutis and N. K. Lassi / Neurotrophins and their receptors in nerve Injury and repairn eurochemistry International // Neurochem Int., 1997, V. 30, pp. 347-374.
Judith A. Siuciak, C. Anthony Altar, Stanley J. Wiegand, Ronald M. Lindsay / Antinociceptive effect of brain-derived neurotrophic factor and neurotrophin-3 // Brain Research, 1994, V. 633, pp. 326-330.
Michiko Ono, Junji Ichihara, Takeshi Nonomura, Yasushi Itakura, Mutsuo Taiji, Chikao Nakayama, and Hiroshi Noguchi / Brain-Derived Neurotrophic Factor Reduces Blood Glucose Level in Obese Diabetic Mice but Not in Normal Mice // Biochem. and Bioph. Res. Commun., 1997, V. 238, pp. 633-637.

(Continued)

*Primary Examiner* — Niloofar Rahmani
(74) *Attorney, Agent, or Firm* — Arent Fox LLP; Michael Fainberg

(57) ABSTRACT

The invention relates to novel alicyclic N,N'-substituted diazabicyclo[3.3.1]nonane derivatives of general formula (I) which act as allosteric AMPA receptor modulators, and to drugs based thereon which can be used for treating Alzheimer's, Parkinson's and other neurodegenerative diseases.

5 Claims, No Drawings

(56) References Cited

OTHER PUBLICATIONS

Brian Villumsen Broberg, Birte Yding Glenthøj, Rebecca Dias, Dorrit Bjerg Larsen, Christina Kurre Olsen / Reversal of cognitive deficits by an ampakine (CX516) and sertindole in two animal models of schizophrenia—sub-chronic and early postnatal PCP treatment in attentional set-shifting // Psychopharmacology, 2009, V. 206, pp. 631-640.

Danielle A. Simmons, Christopher S. Rex, Linda Palmer, Vijay Pandyarajan, Vadim Fedulov, Christine M. Gall, and Gary Lynch // Up-regulating BDNF with an ampakine rescues synaptic plasticity and memory in Huntington's disease knockin mice // Proc. Natl. Acad. Sci. USA, 2009, V. 106, pp. 4906-4911.

Toshiharu Shimazaki, Ayaka Kaku, Shigeyuki Chaki // Blockade of the metabotropic glutamate 2/3 receptors enhances social memory via the AMPA receptor in rats // Eur J Pharmacol., 2007, V. 575, pp. 94-97.

Donald C Goff, J Steven Lamberti, Andrew C Leon, Michael F Green, Alexander L Miller, Jayendra Patel, Theo Manschreck, Oliver Freudenreich and Steven A Johnson / A Placebo-Controlled Add-On Trial of the Ampakine, CX516, for Cognitive Deficits in Schizophrenia // Neuropsychopharmacology, 2008. V. 33, pp. 465-472.

ALICYCLIC DERIVATIVES OF N,N'-SUBSTITUTED 3,7-DIAZABICYCLO[3.3.1]NONANES AND MEDICAMENTS BASED THEREON

This application is a National Stage entry of International Application No. PCT/RU2012/000267, filed on Apr. 10, 2012, which claims priority to and the benefit of Russian Application No. 2011116323, filed on Apr. 26, 2011. The entire content of these prior applications is incorporated herein by reference.

FIELD

This invention relates generally to novel derivatives of N,N'-substituted diazabicyclononanes which are potentially capable of allosteric modulation of AMPA (2-amino-3-(3-hydroxy-5-methylisoxazol-4-yl)propionic acid) receptors. More specifically, the present invention relates to novel pharmacologically active alicyclic derivatives of N,N'-substituted 3,7-diazabicyclo[3.3.1]nonanes which may be employed for the treatment of Alzheimer's disease (AD), Parkinson's disease (PD) and other neurodegenerative pathologies. The present invention also relates to medicaments containing said compounds.

PRIOR ART

The glutamatergic system, to which the AMPA receptors belong, is a primary excitatory neuromediator system in the brain of mammals, including humans, and participates in the implementation of a whole series of physiological and pathological processes. It is known that a wide range of psycho-neurological illnesses, such as PD, AD and similar neurodegenerative disorders, is associated with disruption of the regulation of these processes [Doble A. Pharmacology and Therapeutics, 1999, 81, (3), 163-221].

AMPA receptors are unevenly distributed in the brain. A high concentration of these receptors was found in the superficial layers of the neocortex and in the hippocampus [Monaghan, Brain Res., 1984, 324, 160-164]. Studies in animals and man have shown that these structures are mainly responsible for sensorimotor processes and are a matrix for highly behavioral reactions. Signals in the neurological networks of the brain, responsible for all of the cognitive processes, are thus transmitted due to AMPA receptors.

For the reasons set out above, medicaments which enhance the functioning of AMPA receptors participate in the regulation of processes which form memory, and also processes responsible for the recovery of nerve cells. It has been demonstrated in experiments [Arai, Brain Res., 1992, 598, 173-184] that enhancing the AMPA-mediated synaptic response function increases induction of long-term potentiation (LTP). There is much evidence that LTP, reflecting increase in the strength of synaptic contacts, which ensures constant physiological activity in the brain, is the physiological basis of memory and learning processes. For example, substances which block LTP hinder memory mechanisms in animals and humans [Cerro, Neuroscience, 1992, 46, 1-6].

Substances which enhance the function of AMPA receptors, promoting LTP induction, can favorably influence cognitive function [Granger, Synapse, 1993, 15, 326-329; Arai, Brain Res., 638, 343-346].

Many compounds which activate AMPA receptors are now known. Aniracetam may be taken as an example [Ito, J. Physiol., 1990, 424, 533-543]. It was demonstrated that aniracetam enhances the synaptic signal at several hippocampus sites, while having no effect on NMDA-mediated signals [Staubli, 1990, Psychobiology, 18, 377-381; Xiao, Hippocampus, 1991, 1, 373-380]. One of the features of this preparation is that its effect is short-term. When used peripherally, it is converted into anisoyl-GABA (about 80% of the drug), which itself has no aniracetam-like effects [Guenzi, J. Chromatogr., 1990, 530, 397-406]. The clinical effect of aniracetam is manifested only when it is used in high concentrations (0.1 mM).

A class of substances which in their physiological effect are allosteric modulators of AMPA receptors was discovered comparatively recently. These compounds are more stable and more effective than those previously known, as has been demonstrated in experiments [Staubli, PNAS, 1994, 91, 11158-11162].

In connection with the rapid development of research related to investigation of the pharmacological effect of similar compounds, the experimental fact has recently been established that the intense ionic current which is induced by the action of such allosteric modulators on AMPA receptors, with subsequent depolarization of the post-synaptic membrane, triggers the mechanism of expression of genes responsible for the synthesis of the neurotrophins NGF (nerve growth factor) and BDNF (brain-derived neurotrophic factor)—neural tissue growth factors [Legutko B., Neuropharmacology, 2001, 40, 1019-1027; Ebadi, Neurochemistry International, 2000, 30, 347-374]. The process of expression of genes responsible for neurotrophin synthesis is of enormous importance in the treatment of neurodegenerative disorders and other psycho-neurological diseases. Thus, BDNF has been shown to have an antidepressant effect in behavioral models [Siuciak, Brain Research, 1994, 633, 326-330] and to reduce the blood glucose concentration in mice suffering from diabetes [Ono, J. Biochem. and Bioph. Res. Commun., 1997, 238, 633-637].

In contrast to known stimulants (caffeine, methylphenidate (Ritalin) and amphetamine), ampakines do not elicit such long-term side-effects as insomnia, and are being studied actively as a potential drug to treat brain diseases such as Alzheimer's disease, Parkinson's disease, schizophrenia and other neurological and neurodegenerative disorders. For example, Broberg B. V. et al. (Psychopharmacology, 2004, Apr. 24) demonstrated improvement in cognitive status in schizophrenia when using AMPAkine CX516, while Simmons D. D. et al. (Proc. Natl Acad. Sci. USA, 2009, Mar. 24; 106, (12), 4906-11) established a positive change in cognitive status in Huntington's disease in animal models.

Shimazaki T. et al. (Eur. J. Pharmacol., 2007, Dec. 1; 575, (1-3), 94-7), in an experiment on adult rats, established that compound CX546 in a concentration of 0.3-3 mg/kg improves social memory specifically thanks to positive stimulation of AMPA receptors.

Compound CX516 has become one of the few which have been studied in human patients as a treatment supplementary to antipsychotics in schizophrenia (Goff D. C. et al., Neuropsychopharmacology, 2008 February; 33 (3), 456-72). And although the authors did not observe a significant improvement in the general condition of the patients or in their cognitive status as compared with placebo, they were certain that the search for new and more selective products in this category should be continued.

DISCLOSURE OF THE INVENTION

The invention now proposed is aimed at solving the task of expanding the arsenal of agents which can be employed as novel effective allosteric modulators of AMPA receptors.

As a result of studies performed to search for such compounds, including those triggering the mechanism of expression of genes responsible for the synthesis of neurotrophins—neural tissue growth factors, particularly among compounds having similar activity, the inventors have discovered a broad group of novel derivatives of N,N'-substituted 3,7-diazabicyclo[3.3.1]nonanes in the form of the free bases and salts with pharmacologically acceptable acids, which are together characterized in detail below and constitute one of the aspects of the present invention.

The technical result of the present invention is the creation of novel derivatives of N,N'-substituted 3,7-diazabicyclo[3.3.1]nonanes, including the bases and salts thereof with pharmacologically acceptable acids, which in combination are represented by general formula (1):

wherein:

HY here and hereinafter is a pharmacologically acceptable acid;

E is a carbonyl group;

$R_1$ is H, $C_1$-$C_6$ alkyl or $C_1$-$C_{10}$ alkoxy;

$R_2$ in combination is represented by general formulae (1.1a), (1.2a), (1.3a), (1.4a):

wherein:

L is $CHR_{15}$ or a carbonyl group;

$R_{15}$ is H or $C_1$-$C_6$ alkyl;

M is —NH— or a group with the general formula: —NH—$(CHR_{15})_m$—, where m=0-3;

$R_{15}$ is H or $C_1$-$C_6$ alkyl;

or M is a valence bond;

$R_3$, $R_3'$, $R_4$, $R_4'$, $R_5$, $R_5'$, $R_6$, $R_6'$, $R_7$, $R_7'$, $R_8$, $R_9$, $R_{10}$, $R_{10}'$, $R_{11}$, $R_{11}'$, $R_{12}$, $R_{12}'$, $R_{13}$, and $R_{13}'$ may be the same or different and each independently is H, $C_1$-$C_6$ alkyl or $C_1$-$C_{10}$ alkoxy;

$R_{14}$ is H, $C_1$-$C_6$ alkyl, $C_1$-$C_{10}$ alkoxy, halogen, a nitro group, nitrile, acyl or aryl;

X is a group with the general formula:

where n=0-3, or X is a valence bond;

Z is an atom of oxygen or sulfur.

The term "$C_1$-$C_6$ alkyl" which is used in the definitions given above and in the following description means an alkyl group with a straight or branched chain, containing from 1 to 6 carbon atoms, examples of which are methyl, ethyl, isopropyl, tert-butyl, isopentyl, and similar.

The term "alkoxy" means an AlkO— group, in which the alkyl moiety is the same as the alkyl group specified above. Examples of alkoxy groups include methoxy, butoxy, isopropyloxy and similar groups.

The term "acyl" means a C(O)R group (in which R signifies H, alkyl or aryl as defined above). Examples of acyl groups include formyl, acetyl, benzoyl, phenylacetyl and similar groups.

The term "aryl" signifies an unsubstituted or substituted phenyl or naphthyl group. The substituents of a phenyl group may be halogens (such as fluorine, chlorine and similar), lower alkyl groups (such as methyl, ethyl, isopropyl and similar), or lower alkoxy groups (such as methoxy, ethoxy, isopropoxy and similar). The substituents of a naphthyl group may be fluorine, chlorine, bromine, or methyl and methoxy groups.

The term "pharmacologically acceptable acids" encompasses all pharmacologically acceptable acids, both inorganic (such as hydrochloric, sulfuric, phosphoric, etc.), and organic (such as formic, acetic, oxalic, citric, tartaric, maleic, succinic, p-toluenesulfonic, methylsulfuric, etc.).

PREFERRED EMBODIMENTS OF THE INVENTION

Among the compounds of formula (1) which constitute the subject of the present invention, the following three groups of compounds, which can be represented by formulae (1.1), (1.2) and (1.3), shown below, are preferred. The following compounds are particularly preferred:

1.1. N,N'-substituted 3,7-diazabicyclo[3.3.1]nonanes of general formula (1.1):

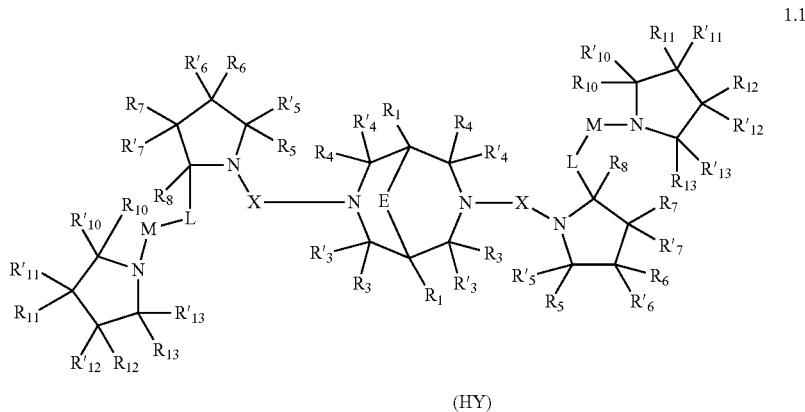

(HY)

1.2. N,N'-substituted 3,7-diazabicyclo[3.3.1]nonanes of general formula (1.2):

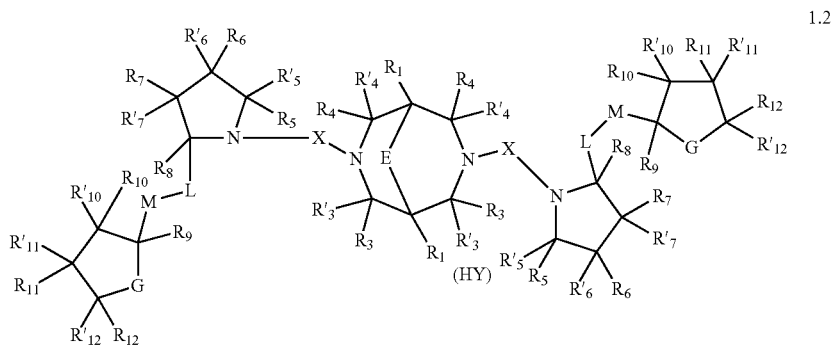

(HY)

1.3 N,N'-substituted 3,7-diazabicyclo[3.3.1]nonanes of general formula (1.3):

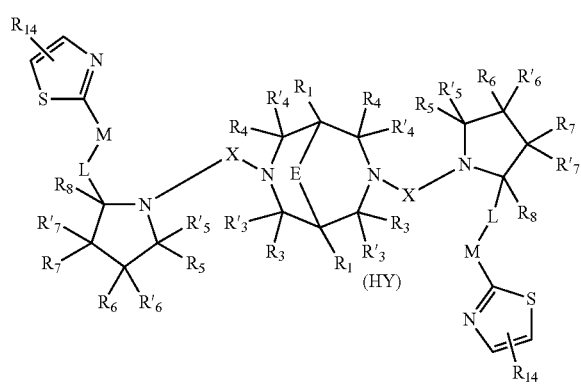

(HY)

1.4. N,N'-substituted 3,7-diazabicyclo[3.3.1]nonanes of general formula (1.4):

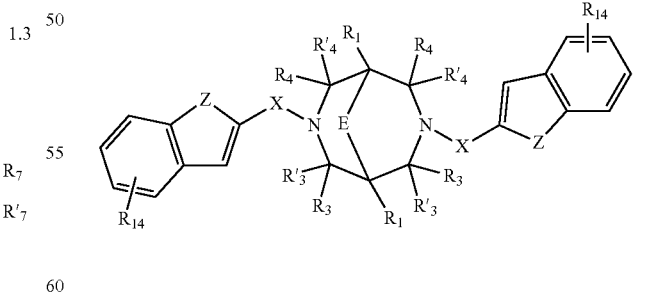

wherein:
HY here and hereinafter is a pharmacologically acceptable acid;
E, $R_1$, $R_3$, $R_3'$, $R_4$, $R_4'$, X, L, M, $R_5$, $R_5'$, $R_6$, $R_6'$, $R_7$, $R_7'$, $R_8$, $R_9$, $R_{10}$, $R_{10}'$, $R_{11}$, $R_{11}'$, $R_{12}$, $R_{12}'$, $R_{13}$, $R_{13}'$ and $R_{14}$ have the meanings specified above for formula 1.

The most preferred compound of formula 1.1 (in the form of pharmacologically acceptable salts and/or the free bases) is:

1,5-dimethyl-3,7-bis{[2-(pyrrolidin-1-yl)prolin-1-yl]acetyl}-3,7-diazabicyclo[3.3.1]nonan-9-one.

The most preferred compound of formula 1.2 (in the form of pharmacologically acceptable salts and/or the free bases) is:

N,N'-[(1,5-dimethyl-9-oxo-3,7-diazabicyclo[3.3.1]nonan-3,7-diyl)bis(2-oxoethane-2,1-diyl)]bis[N-(tetrahydrofuran-2-ylmethyl)proline].

The most preferred compound of formula 1.3 (in the form of a pharmacologically acceptable salt and/or the free base) is:

N,N'-[(1,5-dimethyl-9-oxo-3,7-diazabicyclo[3.3.1]nonan-3,7-diyl)bis(2-oxoethane-2,1-diyl)]bis(N-1,3-thiazol-2-yl-prolinamide).

The most preferred compounds of formula 1.4 (in the form of pharmacologically acceptable salts and/or the free bases) are:

1,5-dimethyl-3,7-bis(1-benzothien-2-ylcarbonyl)-3,7-diazabicyclo[3.3.1]nonan-9-one, 1,5-dimethyl-3,7-bis(5-methoxy-1-benzothien-2-ylcarbonyl)-3,7-diazabicyclo[3.3.1]nonan-9-one, 1,5-dimethyl-3,7-bis(6-bromo-1-benzothien-2-ylcarbonyl)-3,7-diazabicyclo[3.3.1]nonan-9-one.

The invention is described in more detail below with the aid of examples of the preparation of particular compounds.

The starting reagents, and also the final products, are prepared by methods known in the literature or are commercially available.

Schemes for the Synthesis of the Final Compounds are Presented Below

Scheme 1:

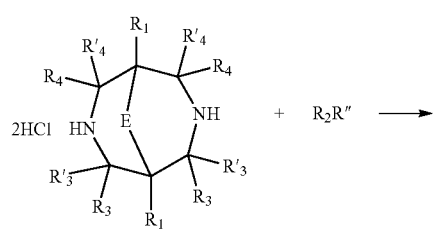

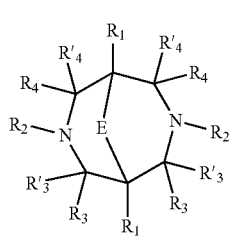

Scheme 2:

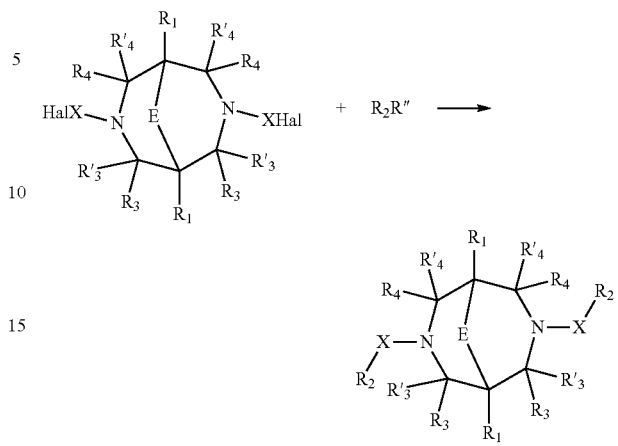

Where in the case of scheme 1 R" is a halogen or a hydroxy group, while in the case of scheme 2 R" is an amino group.

The structures of the compounds prepared were confirmed by the results of chemical and spectral analyses and other physico-chemical characteristics.

Preferred Exemplary Embodiment of the Invention

The examples given below illustrate but do not limit this invention.

Example 1

1,5-dimethyl-3,7-bis{[2-(pyrrolidin-1-yl)-prolin-1-yl]acetyl}-3,7-diazabicyclo[3.3.1]nonan-9-one White crystalline substance. The crystals may be acicular. Yield 82%.

PMR spectrum (CDCl$_3$ δ, ppm): 1.2 (s, 6H), 1.9 (m, 14H), 2.2, (m, 2H), 2.5 (m, 2H), 2.9 (m, 4H), 3.2 (m, 10H), 3.4 (m, 4H), 3.7 (m, 2H), 4.3 (m, 4H).

Example 2

N,N'-[(1,5-dimethyl-9-oxo-3,7-diazabicyclo[3.3.1]nonan-3,7-diyl)bis(2-oxoethane-2,1-diyl)]bis[N-(tetrahydrofuran-2-ylmethyl)proline]

White crystalline substance. The crystals may be lamellar. Yield 76%.

PMR spectrum (CDCl$_3$ δ, ppm): 1.2 (m, 10H), 1.5 (m, 2H), 1.8 (m, 8H), 2.2 (m, 2H), 2.5 (m, 2H), 2.9 (m, 4H), 3.1 (m, 6H), 3.4 (m, 2H), 3.7 (m, 8H), 4.0 (m, 2H), 4.3 (m, 4H).

Example 3

N,N'-[(1,5-dimethyl-9-oxo-3,7-diazabicyclo[3.3.1]nonan-3,7-diyl)bis(2-oxoethane-2,1-diyl)]bis(N-1,3-thiazol-2-ylprolinamide)

White crystalline substance. The crystals may be acicular. Yield 85%.

PMR spectrum (CDCl$_3$ δ, ppm): 1.2 (s, 6H), 1.8 (m, 6H), 2.2 (m, 2H), 2.5 (m, 2H), 2.9 (m, 4H), 3.1 (m, 6H), 3.8 (m, 2H), 4.3 (m, 4H), 7.3 (d, J=3.9 Hz, 2H), 7.5 (d, J=3.9 Hz, 2H).

Example 4

3,7-bis(5-methoxy-1-benzothien-2-yl-carbonyl)-1,5-dimethyl-3,7-diazabicyclo[3.3.1]nonan-9-one White crystalline substance. The crystals may be acicular. Yield 80%.

PMR spectrum (CDCl$_3$ δ, ppm): 1.3 (s, 6H), 2.9 (d, J=12.7 Hz, 2H), 3.6 (d, J=12.7 Hz, 2H), 4.3 (d, J=12.7 Hz, 2H), 4.6 (s, 3H), 5.3 (d, J=12.7 Hz, 2H), 7.2-7.4 (m, 4H), 7.8 (s, 2H), 7.9-8.0 (m, 4H).

Example 5

3,7-bis(1-benzothien-2-ylcarbonyl)-1,5-dimethyl-3,7-diazabicyclo[3.3.1]nonan-9-one White crystalline substance. The crystals may be acicular. Yield 72%.

PMR spectrum (CDCl$_3$ δ, ppm): 1.3 (s, 6H), 2.9 (d, J=12.7 Hz, 2H), 3.6 (d, J=12.7 Hz, 2H), 4.3 (d, J=12.7 Hz, 2H), 5.3 (d, J=12.7 Hz, 2H), 7.2-7.4 (m, 3H), 7.8 (s, 2H), 7.9-8.0 (m, 3H).

Example 6

3,7-bis(6-bromo-1-benzothien-2-ylcarbonyl)-1,5-dimethyl-3,7-diazabicyclo[3.3.1]nonan-9-one White crystalline substance. The crystals may be lamellar. Yield 79%.

PMR spectrum (CDCl$_3$ δ, ppm): 1.3 (s, 6H), 2.9 (d, J=12.7 Hz, 2H), 3.6 (d, J=12.7 Hz, 2H), 4.3 (d, J=12.7 Hz, 2H), 5.3 (d, J=12.7 Hz, 2H), 7.2-7.4 (m, 2H), 7.8 (s, 2H), 7.9-8.0 (m, 3H).

INDUSTRIAL APPLICABILITY

The invention relates to novel alicyclic derivatives of N,N'-substituted 3,7-diazabicyclo[3.3.1]nonanes which have pharmacological activity and may be employed for the treatment of Alzheimer's disease (AD), Parkinson's disease (PD) and other neurodegenerative pathologies.

The invention claimed is:

1. A compound of general formula 1, or a pharmacologically acceptable acid or salt thereof:

wherein:
E is a carbonyl group;
$R_1$ is H, $C_1$-$C_6$ alkyl or $C_1$-$C_{10}$ alkoxy;
$R_2$ is a group of general formula (1.1a):

wherein:
L is —C(HR$_{15}$)— or a carbonyl group;
$R_{15}$ is H or $C_1$-$C_6$ alkyl;
M is —NH— or a group with the general formula: —NH—(CHR$_{15}$)$_m$—, where m equals 0, 1, 2 or 3;
or M is a valence bond;
$R_3$, $R_{3'}$, $R_4$, $R_{4'}$, $R_5$, $R_{5'}$, $R_6$, $R_{6'}$, $R_7R_{7'}$, $R_8$, $R_9$, $R_{10}$, $R_{10'}$, $R_{11}$, $R_{11'}$, $R_{12}$, $R_{12'}$, $R_{13}$, and $R_{13'}$ are identical or different, and each independently is H, $C_1$-$C_6$ alkyl or $C_1$-$C_{10}$ alkoxy;
X is a group with the general formula:

where n equals 0, 1, 2 or 3,
or X is a valence bond.

2. The compound of claim 1, wherein said compound has a general formula (1.1):

wherein:

E, $R_1$, $R_3$, $R_{3'}$, $R_4$, $R_{4'}$, X, L, M, $R_5$, $R_{5'}$, $R_6$, $R_{6'}$, $R_7$, $R_{7'}$, $R_8$, $R_{10}$, $R_{10'}$, $R_{11}$, $R_{11'}$, $R_{12}$, $R_{12'}$, and $R_{13}$, $R_{13'}$ are as defined in claim 1.

3. The compound of claim 2, wherein said compound is 1,5-dimethyl-3,7-bis{[2-(pyrrolidin-1-yl)prolin-1-yl]acetyl}-3,7-diazabicyclo[3.3.1]nonan-9-one.

4. A pharmaceutical composition comprising: the compound of claim 1 and an additive.

5. The pharmaceutical composition according to claim 4 wherein the additive is a pharmacologically acceptable acid.

* * * * *